United States Patent [19]

Colling, Jr. et al.

[11] Patent Number: 5,135,871

[45] Date of Patent: Aug. 4, 1992

[54] METHOD FOR ISOLATING KEROGEN FROM A MINERAL SAMPLE IN A PRESSURIZED REACTION CELL

[75] Inventors: Edwin L. Colling, Jr., Sugarland; David G. Nolte, Houston, both of Tex.

[73] Assignee: Texaco, Inc., White Plains, N.Y.

[21] Appl. No.: 459,486

[22] Filed: Jan. 2, 1990

[51] Int. Cl.$^5$ ............... G01N 1/00; G01N 31/00; C10G 1/04

[52] U.S. Cl. ............... 436/178; 436/31; 208/391; 208/430

[58] Field of Search ............... 436/29, 30, 31, 178; 208/391, 430, 435, 404; 44/620, 621, 624

[56] References Cited

U.S. PATENT DOCUMENTS

| | | | |
|---|---|---|---|
| 4,051,022 | 9/1977 | Myers et al. | 208/253 |
| 4,069,140 | 1/1978 | Wundgerlich | 208/251 X |
| 4,545,891 | 9/1985 | Meyers et al. | 208/404 |
| 4,584,088 | 4/1986 | McCollum et al. | 208/430 |
| 4,668,380 | 5/1987 | Wolff et al. | 208/430 |
| 4,743,271 | 5/1988 | Kindig et al. | 44/621 |
| 4,804,390 | 2/1989 | Lloyd et al. | 44/621 |

OTHER PUBLICATIONS

McCabe et al., in Unit Operations of Chemical Engineering 3rd Ed. (1976) p. 161 and 167.

Durand et al. in Kerogen-Insoluble Organic Matter from Sedimentary Rocks (1980) pp. 35, 50–53.

*Primary Examiner*—James C. Housel
*Assistant Examiner*—William Chan
*Attorney, Agent, or Firm*—Jack H. Park; Kenneth R. Priem; Harold J. Delhommmer

[57] ABSTRACT

A method for isolating kerogen from a mineral sample in a pressurized reaction cell, which permits reaction at pressures greater than two atmospheres and provides for the removal of all liquids from the cell without significant loss of sample solids, employing multiple steps of addition and removal of concentrated hydrochloric acid, concentrated hydrofluoric acid, concentrated ammonium hydroxide, and deionized water.

20 Claims, No Drawings

METHOD FOR ISOLATING KEROGEN FROM A MINERAL SAMPLE IN A PRESSURIZED REACTION CELL

BACKGROUND OF THE INVENTION

This invention is related to a method for isolating kerogen from rock samples. More particularly, the invention is concerned with a method useful for isolating kerogen in a pressurized reaction cell which provides for the removal of all liquids from the cell without significant loss of sample.

Geochemical analysis has become an important part of petroleum exploration over the last two decades. Of key importance to the understanding of the geochemistry of the depositional setting is the analysis of bitumen and kerogen fractions found in sedimentary rock.

There are numerous definitions of bitumen and kerogen. Bitumen will be defined herein as the fraction of sedimentary organic matter which is soluble in organic solvents at moderate temperatures under about 70° C. Compounds extracted in this manner by chloroform, benzene, methanol-benzene mixture, tetrahydrofuran and others are simple hydrocarbons and more complex products which may be heteroatomic and have a high atomic weight such as resins and asphaltenes. This bitumen should not be confused with road bitumen. Road bitumen is an asphalt preparation. Bitumen as used herein is the organic matter within rocks that is soluble in the usual organic solvents.

Kerogen is a solid form of organic matter found in sedimentary rock that is insoluble in water, non-oxidizing acids and bases, and the usual organic solvents. It thermally degrades in a predictable manner by releasing hydrocarbons and condensing the solid organic structure. Because of its immobility, it can provide direct historical evidence of geological conditions within a stratigraphic sequence.

Characterization of kerogen, the precursor to oil and gas, is essential in determining the potential of a rock unit to generate hydrocarbons. The study of kerogen is accomplished by first isolating the kerogen from its rock matrix, and then studying its morphology by several methods, including transmitted light microscopy, its organic metamorphism or thermal alteration by reflected light microscopy, and its chemistry by elemental, isotopic and pyrolysis methods.

Kerogen must be isolated in such a way that the isolated fraction is as representative as possible of in situ kerogen. Analysis requires the recovery of a sufficient amount of kerogen sample without chemical alteration. A principle objective is to keep the morphology of the kerogen intact and to recover identifiable organic debris.

The isolation of kerogen is a complicated chemical process that involves the use of strong acids and bases that dissolve the rock matrix without modifying the kerogen. The rock sample is first finely ground in order to facilitate reaction with the reagents. The methods now used for kerogen isolation employ the dissolution of silicates by hydrofluoric acid and the dissolution of sulfides, sulphates, carbonates, oxides and hydroxides by hydrochloric acid. The reactions are normally carried out below 70° C., a temperature sufficient to dissolve carbonates, but inadequate to promote oxidation and degradation of the organic matter. For a general discussion of the methods of kerogen isolation and reagents employed, please see Durand, B. and Nicaise, G., "Chapter Two-Procedures for Kerogen Isolation," within *Kerogen*, edited by Durand, B., Graham & Trotman Ltd, London (1980) p. 35-52.

Generally the acid and base reactions are carried out in open plastic beakers placed in a steam bath to raise reaction temperature. After reaction, the aqueous liquids are removed from the beakers by decanting. The reaction steps are repeated until kerogen isolation is judged to be relatively complete. This usually takes anywhere from two to four weeks depending on the quality requirements of subsequent analyses and the type of rock being dissolved.

The process of decanting as well as the length of the procedure leaves much to be desired. A disadvantage to current isolation techniques is that a percentage of the kerogen is frequently lost during decanting. Second, since aqueous liquids are never completely removed from the beakers, solvated metal and silicate ions are available as reactants to form fluoride precipitates. Once precipitated, these neoformed fluorides are virtually impossible to dissolve and remove without damaging the remaining kerogen. Third, beakers permit exposure to oxygen which creates undesirable oxidation products.

An additional step is often required for the final separation of kerogen from unreacted minerals and precipitates. A high density solution of zinc bromide is frequently mixed with the kerogen to cause the lower density kerogen to float. The floated kerogen is decanted and water washed prior to subsequent analyses. Unfortunately, this causes further fractionation and loss of kerogen which lowers the quality and representativeness of the isolated kerogen sample relative to its in situ form in the original rock.

Other difficulties exist with current kerogen isolation procedures. Dangers to the workers who perform kerogen and bitumen isolation in the standard open beaker method include exposure to hazardous highly concentrated hydrofluoric and hydrochloric acids and bases such as ammonium hydroxide, all of which must be added and decanted manually. Use of such chemicals requires not only protective personal equipment but also engineering controls such as hoods and other vacuum equipment. In addition, chemical solutions containing zinc bromide and organic solvents are environmentally hazardous and require special handling for disposal.

SUMMARY OF THE INVENTION

The invention is a method for the isolation of kerogen from the mineral matrix sample in a pressurized reaction cell which comprises multiple reaction steps between acid and base reagents and the mineral sample placed within a pressurized reaction cell. The reaction cell must permit reaction at pressures greater than about two atmospheres and provide for removal of all liquids from the cell without significant loss of sample solids.

The isolation method starts by adding a mixture of concentrated hydrochloric acid and deionized water to the reaction cell. After the desired period of reaction, the mixture is removed and concentrated hydrochloric acid is added to the reaction cell. After the desired reaction time, the hydrochloric acid is removed from the reaction cell and the reaction cell is flushed with deionized water to remove any remaining metal ions and to bring the sample relatively close to neutrality.

Concentrated ammonium hydroxide is added to the reaction cell, allowed to react for the desired time and removed from the reaction cell. The reaction cell is then flushed with deionized water. Concentrated hydrofluoric acid is added to the reaction cell for the desired reaction time and then removed. Concentrated hydrochloric acid is added to the reaction cell and removed. The reaction cell is flushed with deionized water.

Concentrated ammonium hydroxide is added to the reaction cell and removed prior to flushing the reaction cell with deionized water once again. Finally, the kerogen is left immersed in deionized water to maintain the kerogen in the hydrated condition for analysis.

DETAILED DESCRIPTION

The present technology for isolating kerogen involves complex manual processing of rock materials using the combination of acids, bases, reducing agents and organic solvents. The process is intended to isolate kerogen without damaging the organic matter in the process. Current procedure is tied to the use of manual isolation process steps involving beakers open to the atmosphere and requiring decanting of all fluids after settling of the samples for each reagent addition step. The lengthy time of about two to four weeks required to isolate kerogen with presently known processes is perhaps the most notable disadvantage. The instant invention process employed with the pressurized reaction cell permitting complete removal of liquids offers a process which can isolate kerogen in about 24 hours.

The invention method requires first placing the mineral sample in a reaction cell, said reaction cell permitting reaction at pressures greater than about two atmospheres and providing for removal of all liquids from the cell without significant loss of sample solids. It is preferred that the reaction cell provide for the removal of reagents and dissolve materials by drainage through a filter at the bottom of the reaction cell.

It is also preferred that the invention process be run at elevated temperatures of about 45° C. to about 65° C. Such higher reaction temperatures substantially shorten the digestion times needed to isolate kerogen. However, the reaction steps cannot be accomplished at these higher temperatures without maintaining the reaction cell under pressure of at least 2 atmospheres, preferably about 2.5 atmospheres to about 5 atmospheres. At higher temperatures and lower pressures, the concentrated acids and bases required will lose substantial strength through evaporation.

The first step involves adding a mixture of concentrated hydrochloric acid and deionized water to the reaction cell. Preferably the mixture is within the range of about ½ to 3/1 concentrated hydrochloric acid to deionized water, and is allowed to digest for a time greater than about 15 minutes, preferably about 30 minutes at 50° C. to about 60° C. and about 3 atmospheres of pressure. The concentrated hydrochloric acid is preferably about 10 to about 12 molar concentration.

For all reaction steps of the invention, it should be noted that required reaction times will vary greatly depending upon several factors including the concentration of the reagents, the temperature and pressure of the reaction, and the type and the amount of compounds within the mineral sample. For example, a higher reaction temperature may substantially decrease the needed reaction time. Furthermore, preferred reaction times are always longer than required reaction times since it is desirable to have a safe margin in the reaction time to insure removal of undesired compounds from the mineral sample. And when necessary, due to the presence of greater than usual amounts of certain compounds, reaction times may be extended or several groups of process steps may be repeated.

After the desired reaction time, the mixture of concentrated hydrochloric acid and deionized water is removed from the reaction cell to remove highly reactive aragonite, calcites, calcium and magnesium ions. Concentrated hydrochloric acid is then added to the reaction cell for a preferred reaction time greater than about 45 minutes, most preferably about 90 minutes at the desired temperature and pressure ranges of about 3 atmospheres and 50° C. to 60° C. As previously stated, the hydrochloric acid is preferably of a concentration of about 10 to about 12 moles per liter. The hydrochloric acid is removed from the reaction cell to remove slowly reacting carbonates and undesirable metal ions.

The reaction cell is flushed with deionized water to remove any remaining metal ions and to bring the sample relatively close to neutrality. Preferably, the flushing is done continuously for a time greater than about 15 minutes, most preferably for about 30 minutes.

Concentrated ammonium hydroxide is added to the reaction cell for a preferred reaction time greater than about 15 minutes, most preferably about 30 minutes at the most preferred temperature, (50°-60° C.) and pressure ranges (3 atmospheres) stated above. The concentrated ammonium hydroxide preferably has a concentration of about 10 to about 20 moles per liter. The ammonium hydroxide is removed from the reaction cell to remove silicate ions and base soluable inorganics. The reaction cell is then flushed with deionized water as before.

Concentrated hydrofluoric acid is added to the reaction cell for a preferred reaction time greater than about 45 minutes, most preferably about 90 minutes in a preferred concentration of about 25 to about 35 moles per liter. After reaction, the hydrofluoric acid is removed along with dissolved silicate minerals and certain fluorinated compounds.

Concentrated hydrochloric acid is then added to the reaction cell and permitted to react for a time greater than about 45 minutes, most preferably about 90 minutes. The hydrochloric acid is then removed from the reaction cell along with dissolved chlorinated compounds, and the reaction cell is flushed with deionized water.

Concentrated ammonium hydroxide is added to the reaction cell and permitted to react preferably for a time greater than about 15 minutes, most preferably about 30 minutes. The ammonium hydroxide has a preferred concentration of about 10 to about 20 moles per liter. Gel-formed silicas and silicates are removed from the reaction cell along with ammonium hydroxide. The reaction cell is then flushed with deionized water to insure the removal of all liquids and bring the sample close to neutrality. The kerogen is left immersed in deionized water to maintain the kerogen in a hydrated condition for analysis.

In order to insure a more complete and accurate kerogen isolation, the first addition and removal steps of hydrochloric acid before the first flushing of reaction cell with deionized water are preferably repeated. It is also preferred to sequentially repeat all steps after the second deionized water flushing step and before leaving the kerogen immersed in deionized water. This repetition of steps should occur after the fourth deionized water flushing step and before leaving the kerogen immersed in deionized water.

The presence of pyrites in the mineral sample can create substantial problems in kerogen isolation because they are difficult to remove. If the sample is known or suspected to contain pyrites, it is preferred to follow an additional series of process steps to remove the pyrite. These pyrite removal steps are preferably implemented after the fourth flushing of the cell with deionized water and prior to leaving the kerogen immersed in deionized water for study.

To remove pyrites, sodium tetrahydridoborate is added to the reaction cell to reduce pyrite to pyrrhotite. The sodium tetrahydridoborate is preferably permitted to react with the sample for a time greater than about 45 minutes, most preferably about 90 minutes at about 50° C. to about 60° C. at a concentration of about 1 to about 5 moles per liter. The sodium tetrahydridoborate is removed from the reaction cell and concentrated hydrochloric acid is added to the reaction cell to neutralize the remaining sodium tetrahydridoborate and dissolve the newly formed pyrrhotite. This is permitted to digest for a time greater than about 45 minutes, most preferably about 90 minutes at about 50° C. to about 60° C. The hydrochloric acid is removed from the reaction cell and the cell is flushed with deionized water.

It is most preferred to repeat the pyrite removal steps outlined above to insure that all traces of pyrite are removed from the mineral sample. In order to prepare the sample for the repetition of the pyrite removal steps, it is first desirable to add concentrated ammonium hydroxide to the reaction cell for a preferred time greater than about 15 minutes, most preferably about 30 minutes. Sodium tetrahydridoborate is a base and ammonium hydroxide provides the necessary transition step for further treatment with sodium tetrahydridoborate. After addition and removal of ammonium hydroxide, the reaction cell is flushed with deionized water and the above pyrite removal steps involving sodium tetrahydridoborate, hydrochloric acid, water washing, ammonium hydroxide and water washing are repeated.

The mineral sample in the reaction cell is preferably agitated during reaction by injecting an inert gas into the reaction cell. Such agitation insures that the reaction will be more complete and will proceed at a faster rate. The inert gas used for agitation may be helium, argon, neon, and most preferably, nitrogen. The use of such inert gas and a reaction cell and system not exposed to the air will insure that the sample is not exposed to oxygen. Atmospheric exposure can cause varying degrees of oxidation and affect the kerogen ultimately isolated.

Total reaction time of the most preferred method including the double repetition of the pyrite removal steps is approximately 23–24 hours. The inventors employ a reaction cell with an interior volume of about 125 ml. Within that cell a rock sample of about 10g to about 40g is processed. 50 ml of each reagent is added for each step to the reaction cell. This amount is sufficient to completely cover the mineral sample. With the use of 50 ml samples for each addition step, the preferred invention process uses the following volumes and concentrations of reagents to process each mineral sample.

| 350 ml | Hydrochloric Acid | (12M) |
|---|---|---|
| 250 ml | Ammonium Hydroxide | (14M) |
| 100 ml | Hydrofluoric Acid | (29M) |
| 100 ml | Sodium Tetrahydridoborate | (2M) |

The automated apparatus disclosed therein comprises one or more reaction cells, a measuring cell for providing a desired amount of fluid to the reaction cell, at least one sensor in the measuring cell for indicating a desired level of fluid, multiple fluid sources to be used for isolating the mineral samples, a fluid source valve for each fluid source to control the fluid flow from each fluid source to the measuring cell, a reaction cell valve for each reaction cell to control fluid flow between the measuring cell and the reaction cell, said reaction cell valve located between the measuring cell and the reaction cell, a waste dump valve to control fluid flow between the reaction cell and a waste dump, a back pressure regulator to provide for the safe release of excess pressure in the reaction cell and to moderate the reaction by releasing pressure, tubing to provide fluid communication between multiple fluid sources and the measuring cell, tubing to provide fluid communication between the measuring cell and the reaction cell valve, and between the reaction cell valve and the reaction cell, tubing to provide fluid communication between the reaction cell and a waste dump.

The above elements are controlled by a microprocessor control system which sequentially opens and closes the proper valves in the desired order to fill the measuring cell with the desired fluids, discharge the contents of the measuring cell into the reaction cell, and drain the fluid contents of the reaction cell into the waste dump or a fraction collector at the desired times. The reaction cell, measuring cell, valves and tubing are made of materials substantially inert to acidic and basic reagents.

The reaction cell is comprised of a central reaction chamber, a sample retaining means which divides the chamber into upper and lower chambers, a first port communicating with the lower chamber, a first filter means located between the first port and the lower chamber, a second port communicating with the upper chamber, and a second filter means located between the second port and the upper chamber.

The apparatus is ideal for the automated isolation of various compounds from a mineral matrix by the use of acidic and basic reagents to attack the mineral matrix and remove undesirable compounds or minerals, or remove desired compounds or minerals as a solute to be later collected. The apparatus is also useful for gas-solid reactions, gas-liquid reactions, and the acid digestion of rocks and metals. The primary utility of the apparatus is believed to be the initial extraction of bitumen and isolation of kerogen from rock samples.

Many other variations and modifications may be made in the concepts described by those skilled in the art without departing from the concepts of the present invention. Accordingly, it should be clearly understood that the concepts disclosed in the description are illustrative only and are not intended as limitations on the scope of the invention.

What is claimed is:

1. A method for the isolation of kerogen from a mineral sample in a pressurized reaction cell which comprises:
   placing the mineral sample in a reaction cell,
   said reaction cell permitting reaction at pressures greater than about two atmospheres and providing for removal of all liquids from the cell without significant loss of sample solids;

adding a mixture of concentrated hydrochloric acid and deionized water to the reaction cell;

removing the mixture from the reaction cell to remove highly reactive aragonite, calcite, calcium and magnesium ions;

adding concentrated hydrochloric acid to the reaction cell;

removing the hydrochloric acid from the reaction cell to remove dissolved carbonates and undesirable metal ions;

flushing the reaction cell with deionized water to remove any remaining metal ions and bring the sample relatively close to neutrality;

adding concentrated ammonium hydroxide to the reaction cell;

removing the ammonium hydroxide from the reaction cell to remove silicate ions and base soluble inorganics;

flushing the reaction cell with deionized water to remove all ions and bring the sample relatively close to neutrality;

adding concentrated hydrofluoric acid to the reaction cell;

removing the hydrofluoric acid from the reaction cell to remove silicate ions and fluorinated compounds;

adding concentrated hydrochloric acid to the reaction cell;

removing the hydrochloric acid from the reaction cell to remove fluorinated compounds;

flushing the reaction cell with deionized water;

adding concentrated ammonium hydroxide to the reaction cell;

removing the ammonium hydroxide from the reaction cell to remove any gel-formed silicas and silicates;

flushing the reaction cell with deionized water; and leaving the kerogen immersed in deionized water to maintain the kerogen in a hydrated condition for analysis.

2. The method of claim 1, further comprising repeating the addition and removal steps of hydrochloric acid before the first flushing of the reaction cell with deionized water.

3. The method of claim 1, further comprising sequentially repeating all steps after the second deionized water flushing step and before leaving the kerogen immersed in deionized water, said sequential repeating occurring after the fourth deionized water flushing step and before leaving the kerogen immersed in deionized water.

4. The method of claim 1, further comprising:
adding sodium tetrahydridoborate to the reaction cell to reduce pyrite to pyrrhotite, said addition occurring after the last deionized water flushing step and before leaving the kerogen immersed in deionized water;

removing the sodium tetrahydridoborate from the reaction cell;

adding concentrated hydrochloric acid to the reaction cell to neutralize remaining sodium tetrahydridoborate and dissolve the newly formed pyrrhotite;

removing the hydrochloric acid from the reaction cell; and flushing the reaction cell with deionized water.

5. The method of claim 4, further comprising:

adding concentrated ammonium hydroxide to the reaction cell after the last deionized water flushing step and before leaving the kerogen immersed in deionized water;

then removing the ammonium hydroxide from the reaction cell;

flushing the reaction cell with deionized water;

adding and removing from the reaction cell in sequence sodium tetrahydridoborate, concentrated hydrochloric acid, deionized water, and concentrated ammonium hydroxide; and flushing the reaction cell with deionized water.

6. The method of claim 1, further comprising performing the kerogen isolation at an elevated temperature of about 45° to about 65° C.

7. The method of claim 6, wherein said mixture of hydrochloric acid and deionized water is reacted with the sample for a time greater than about 15 minutes.

8. The method of claim 6, wherein the hydrochloric acid is reacted with the sample for a time greater than about 45 minutes.

9. The method of claim 6, wherein the deionized water flushing steps occur for a time greater than about 15 minutes.

10. The method of claim 6, wherein the concentrated ammonium hydroxide is reacted with the sample for a time greater than about 15 minutes.

11. The method of claim 6, wherein the concentrated hydrofluoric acid is reacted with the sample for a time greater than about 45 minutes.

12. The method of claim 1, wherein the kerogen isolation is performed at a pressure of about 2.5 atmospheres to about 5 atmospheres.

13. The method of claim 1, wherein bitumen has been removed from the mineral sample prior to beginning the kerogen isolation.

14. The method of claim 1, wherein the concentrated hydrochloric acid has a concentration of about 10 to about 12 molar.

15. The method of claim 1, wherein the concentrated hydrofluoric acid has a concentration of about 25 to about 35 molar.

16. The method of claim 1, wherein the concentrated ammonium hydroxide has a concentration of about 10 to about 20 molar.

17. The method of claim 4, wherein the sodium tetrahydridoborate has a concentration of about 1 to about 5 molar.

18. The method of claim 1, further comprising agitating the mineral sample in the reaction cell during reaction with added reagents by injecting an inert gas into the reaction cell.

19. The method of claim 18, wherein the inert gas is nitrogen, helium, argon, or neon.

20. A method for the isolation of kerogen from a mineral sample in a pressurized reaction cell which comprises:

placing the mineral sample in a reaction cell;

said reaction cell permitting reaction at pressures greater than about 2 atmospheres and temperatures between about 45° C. and about 65° C., and providing for removal of all liquids from the cell without significant loss of sample solids;

adding a mixture of concentrated hydrochloric acid and deionized water to the reaction cell and permitting reaction for a time greater than about 15 minutes at about 45° C. to about 65° C.;

removing the mixture from the reaction cell to remove highly reactive aragonite, calcite, calcium and magnesium ions;

adding concentrated hydrochloric acid to the reaction cell and permitting reaction for a time greater than about 45 minutes at about 45° C. to about 65° C.;

removing the hydrochloric acid from the reaction cell to remove slowly reacting carbonates and undesirable metal ions;

flushing the reaction cell with deionized water to remove any remaining metal ions and bring the sample relatively close to neutrality;

adding concentrated ammonium hydroxide to the reaction cell and permitting reaction for a time greater than about 15 minutes at about 45° C. to about 65° C.;

removing the ammonium hydroxide from the reaction cell to remove silicate ions and base soluble inorganics;

flushing the reaction cell with deionized water to remove all ions and bring the sample relatively close to neutrality;

adding concentrated hydrofluoric acid to the reaction cell and permitting reaction for a time greater than about 45 minutes at about 45° C. to about 65° C.;

removing the hydrofluoric acid from the reaction cell to remove silicate ions and fluorinated compounds;

adding concentrated hydrochloric acid to the reaction cell and permitting reaction for a time greater than about 45 minutes at about 45° C. to about 65° C.;

removing the hydrochloric acid from the reaction cell to remove fluorinated compounds;

flushing the reaction cell with deionized water;

adding concentrated ammonium hydroxide to the reaction cell and permitting reaction for a time greater than about 15 minutes at about 45° C. to about 65° C.;

removing the ammonium hydroxide from the reaction cell to remove any gel-formed silicas and silicates;

flushing the reaction cell with deionized water;

adding sodium tetrahydridoborate to the reaction cell to reduce pyrite to pyrrhotite and permitting reaction for a time greater than about 45 minutes at about 45° C. to about 65° C.;

removing the sodium tetrahydridoborate from the reaction cell;

adding concentrated hydrochloric acid to the reaction cell to neutralize remaining sodium tetrahydridoborate and dissolve the newly found pyrrhotite in the reaction cell and permitting reaction for a time greater than about 45 minutes at about 45° C. to about 65° C.;

removing the hydrochloric acid from the reaction cell;

flushing the reaction cell with deionized water;

adding concentrated ammonium hydroxide to the reaction cell and permitting reaction for a time greater than about 15 minutes at about 45° C. to about 65° C.;

removing the ammonium hydroxide from the reaction cell;

flushing the reaction cell with deionized water;

then repeating all of the above steps starting with the addition of sodium tetrahydridoborate and ending with the removal of ammonium hydroxide and flushing with deionized water; and leaving the kerogen immersed in deionized water to maintain the kerogen in a hydrated condition for analysis.

* * * * *